United States Patent [19]
Balfour et al.

[11] Patent Number: 5,368,480
[45] Date of Patent: Nov. 29, 1994

[54] DENTAL IMPLANT WRENCH

[75] Inventors: Alan R. Balfour, Camarillo; Daniel R. Patrick, El Segundo, both of Calif.

[73] Assignee: Dentsply Research & Development Corp., Milford, Del.

[21] Appl. No.: 163,615

[22] Filed: Dec. 8, 1993

[51] Int. Cl.5 .................................................. A61C 3/00
[52] U.S. Cl. ...................................... 433/141; 433/174; 81/471
[58] Field of Search ............... 433/141, 163, 174, 225; 81/52, 467, 471, 473, 474, 475, 476, 478

[56] References Cited
U.S. PATENT DOCUMENTS

| | | |
|---|---|---|
| 881,075 | 3/1908 | Hosking . |
| 2,948,173 | 8/1960 | Herrmann ........................ 81/474 |
| 3,191,486 | 6/1965 | Gibbens . |
| 3,279,286 | 11/1966 | Larson . |
| 3,331,267 | 7/1967 | Tietge . |
| 3,425,314 | 2/1969 | Ohlson . |
| 4,177,562 | 12/1979 | Miller et al. . |
| 4,215,600 | 8/1980 | Kesselman . |
| 4,553,942 | 11/1985 | Sutter ................................ 433/225 |
| 4,645,453 | 2/1987 | Niznick . |
| 4,649,727 | 3/1987 | Gray . |
| 4,682,520 | 7/1987 | Gray . |
| 4,687,392 | 8/1987 | Bidwell . |
| 4,833,951 | 5/1989 | Karcher et al. . |
| 4,976,617 | 12/1990 | Carchidi . |
| 5,078,607 | 1/1992 | Niznick . |
| 5,158,458 | 10/1992 | Perry . |
| 5,176,050 | 1/1993 | Sauer et al. . |

OTHER PUBLICATIONS

5 Pages Literature regarding Nova-Hex.
Engineering a Device for Installing Dental Implants, pp. 72 & 73, Apr. 1992/Mechanical Engineering.
Oral Surgical Mini-Ratchet, 1 page.
Nobelpharma Torque Controller, 2 Pages.
A New Branemark Single Tooth Abutment: Handling and Early Clinical Experiences, from The Journal of Oral & Maxiloracial Implant, 3 Pages.
Achieving Ideal Esthetics in Osseointegrated Prostheses. Part II. The Single Unit. Abstract, 4 Pages.

*Primary Examiner*—Cary E. O'Connor
*Attorney, Agent, or Firm*—Edward J. Hanson, Jr.

[57] ABSTRACT

A low profile dental torque ratchet system is provided having a disposable breakaway color coded insert for holding a tool to be driven by a torsional ratchet wrench. Incorporated within the ratchet wrench is a driver that drives the tool until a preset torsional force shears the insert.

13 Claims, 3 Drawing Sheets

5,368,480

DENTAL IMPLANT WRENCH

TECHNICAL FIELD

The present invention relates generally to restorative dentistry and more particularly to a torque control system for use when driving and tightening components used in a dental prosthodontic restoration especially those involving dental implants.

BACKGROUND OF THE INVENTION

Prosthodontic restorative systems and techniques are well-known in the prior art. For partially or fully edentulous patients, a dental implant fixture is implanted in a cylindrical bore made in the alveolar ridge crest of a patient's jawbone after the gum tissue has been displaced. The fixture typically includes an internally-threaded cylindrical socket which receives one or more components used for attaching a permanent dental restoration to the fixture. The components typically include an abutment base in the form of a short tubular body having a transverse wall at a first end thereof shaped to mate with the gingival aspect of a transverse surface of the implant fixture. The abutment base has a bore therethrough for receiving an abutment screw used to retain the abutment base to the fixture. A coping is retained in the abutment screw using a coping screw. A dental restoration, in the form of an anatomical overlay, is adapted to be fabricated to the coping. Such systems are shown in U.S. Pat. Nos. 4,645,453 and 5,078,607 to Niznick.

The various components of the dental prosthodontic restoration are typically driven and tightened with respect to the implant mixture or each other using a plurality of different drivers, one for each type of component. The prosthodontist manipulates the drivers manually or through the use of an automatic device.

Precise and complete tightening of the components in a restoration is often difficult to achieve manually. Thus, the components often loosen and back-out of their fittings, requiring repeated office visits for the retightening. To combat the loosening or unscrewing of the implant/prosthetic system a pre-determined pre-load needs to be applied to the engaged threads. To accomplish this process several torsional ratchet tools have been designed. Of these tools, a few incorporate a breakaway feature to generate the desired torque and prevent the seating tool or screw from stripping. Although these breakaway ratchets meet the desired functional requirements, due to wear they do not maintain their calibration after continuous use. Furthermore, incorporating this breakaway feature into the available ratchets has made the final tool's cost, size, sterility and ease of use prohibitive as the systems contain many intricate moving components. An attempt to overcome many of the shortcomings of the prior art is shown in U.S. Pat. No. 5,158,458 which employs a torque element having a plurality of spokes, all of which break to provide the torque limit.

There is therefore a need to provide a new system for driving components used in a dental prosthodontic restoration that overcomes these and other problems of the prior art.

BRIEF SUMMARY OF THE INVENTION

It is an object of the present invention to provide a system for driving components of a dental restoration system that precisely and reproducibly tightens components to a specified torque in a simple and cost effective way.

It is a further object of the invention to provide a system that allows for sequentially tightening a plurality of components requiring identical torque without re-loading the torque control.

It is yet another object of the invention to provide such a system that is simple and easy-to-use, and that can be driven manually (e.g., by finger grip or rachet) or automatically (e.g., by a handpiece).

It is still another object to provide a system for driving components in a dental restoration system that can be used with a variety of different makes and styles of component parts.

It is yet a further object to provide such a system that has little or no maintenance and which includes disposable elements for exacting torque control reliability.

These and other objects of the invention are provided in a system for driving and tightening components used in dental prosthodontic restoration providing a ratchet wrench with a plurality of interchangeable tools and a plurality of torque control elements, each of the torque control elements having a predetermined torque rating.

The foregoing outlines some of the pertinent objects of the present invention. These objects should be construed to be merely illustrative of some of the more prominent features and applications of the invention. Many other beneficial results can be attained by applying the disclosed invention in a different manner or modifying the invention. Accordingly, other objects and a fuller understanding of the invention may be had by referring to the following Detailed Description of the preferred embodiment.

PREFERRED EMBODIMENT

Figure 1:
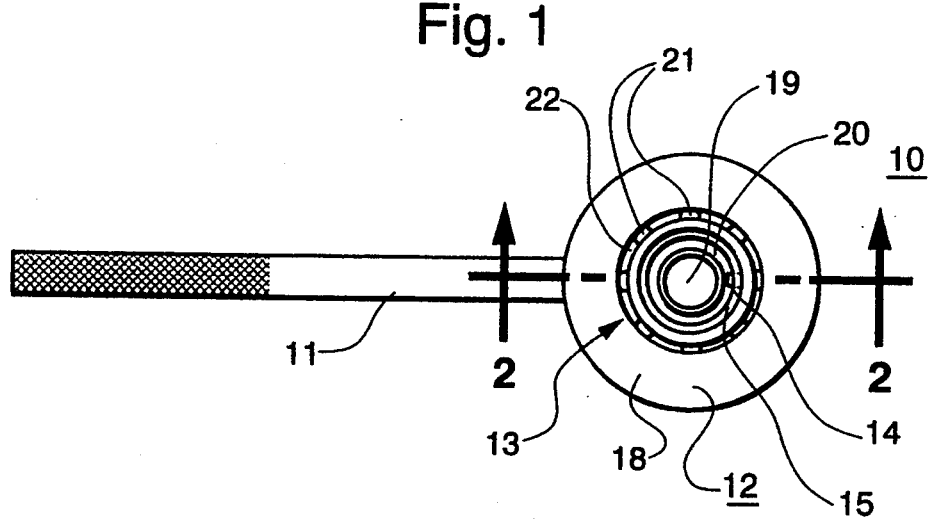
FIG. 1 is a plan view of the basic ratchet device.

Referring to FIG. 1, a ratchet wrench 10 is shown. The ratchet wrench 10 has a ratchet handle 11 and a ratchet head 12. The ratchet wrench is of a standard type of ratchet wrench mechanism except for the tool holder mounting unit 13. The tool holder mounting unit has a driver pin paddle blade 14 carried by a driving sleeve 9, see FIG. 2 also. The driver 14 drives the tool during use of the ratchet wrench 10.

Figure 2:
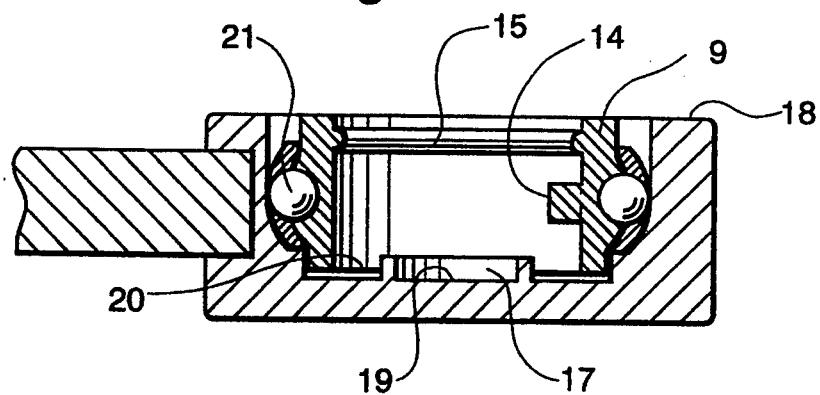
FIG. 2 is an enlarged sectional view through the ratchet unit taken on the line 2—2 of FIG. 1.
Figure 5:
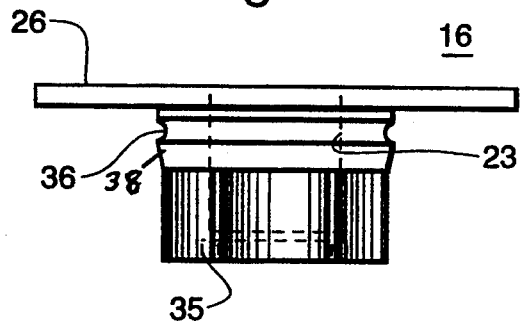
Figure 7:
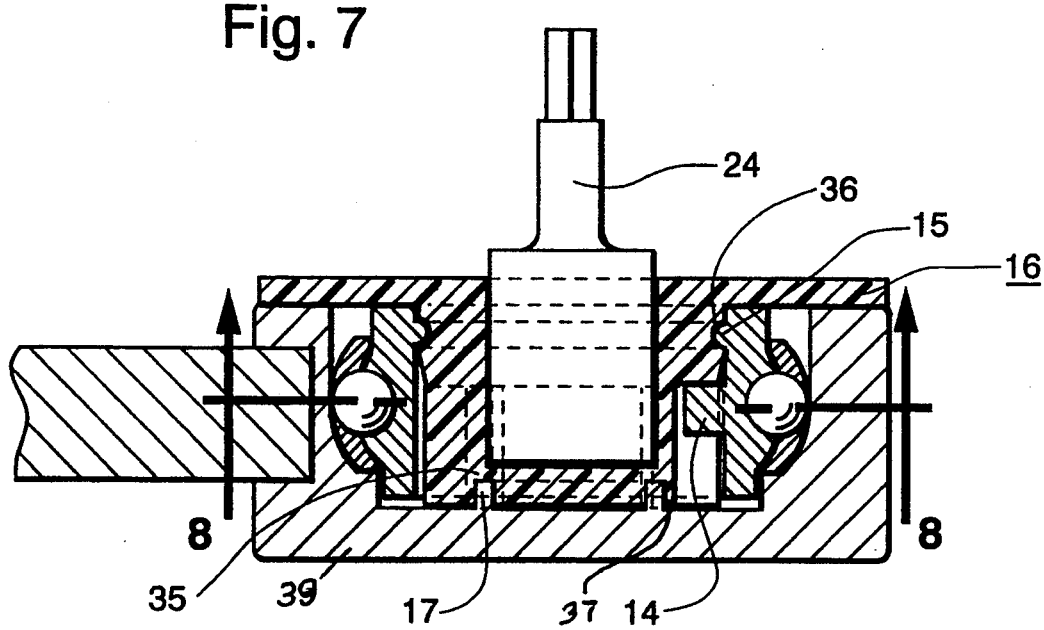
FIG. 7 is a sectional view similar to FIG. 2, but showing the various parts in assembled relationship.

Looking at FIGS. 1 and 2 the tool holder mounting unit may be seen to have a snap retention journaling rim ring 15 for retaining the tool adaptor 16, FIGS. 5 and 7. A journaling seat ring 17 is also shown. The journaling members journal the tool holder for rotation of the ratchet wrench when it is released for reset and further rotation of the tool and also for slippage when the torque limit is reached. Outer ratchet wrench face 18 and inside floor 19 within the seat ring 17 and inside floor 20 outside of the seat ring 17, are also seen in FIGS. 1 and 2. Conventional ratchet parts such as ball bearings 21 and race 22 are also shown.

Figure 3:
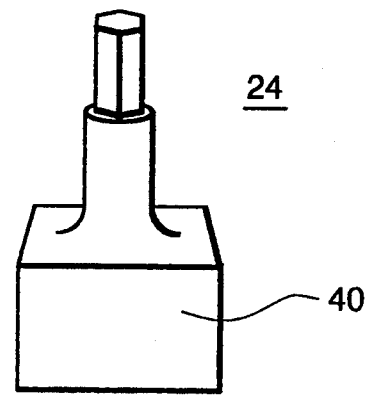
FIG. 3 is a perspective of a hex wrench unit for use with the ratchet of FIGS. 1 and 2.

Turning now to the tool adaptor 16 which is a dental tightening torque limit tool holder, it will be seen that the tool adaptor 16 has a concentric tool receiving and mounting aperture or tool fixture 23 which frictionally secures a tool 24, FIGS. 3 and 7, in operable position. Of course, detents and other tool securing means could be used singularly or in combination to secure the tool. The mounting aperture is shown in phantom lines in FIGS. 5 and 6.

The tool adaptor 16 has a torque limit control structure 25 as an integral unitary part thereof. While in its preferred embodiment the torque limiter is a single unitary part with the tool adaptor without having been assembled, it could be an assembly in other embodiments. By a unitary part it is meant that there has been no assembly and the part was made unitarily by, for example, being injection molded as one piece or machined from a single piece or blank. Also while in the preferred embodiment the tool adaptor and torque control are a single unit, it is obvious that in some embodiments it would be preferred to have them separated physically and functionally. In yet other preferred embodiments the tool would be a fixed tool with the torque limiter or the tool could be fixed to the torque wrench and the torque limiter replaceable.

Figure 4:
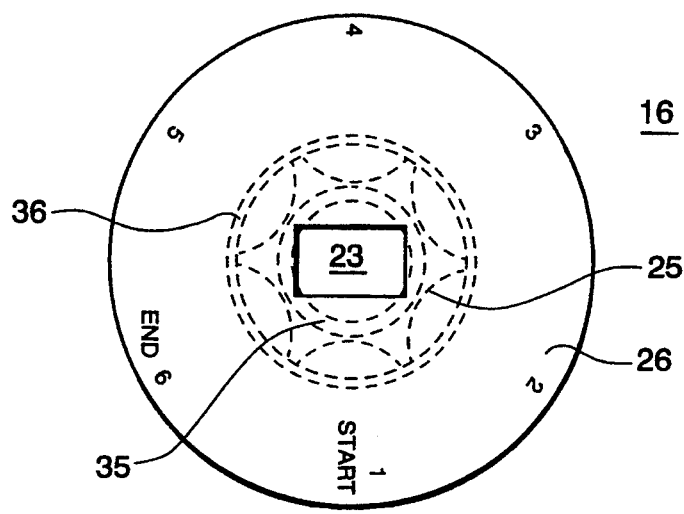
FIGS. 4, 5 and 6 are, respectively, top, side and bottom views of the plastic insert to co-act with the ratchet and wrench units.
Figure 6:
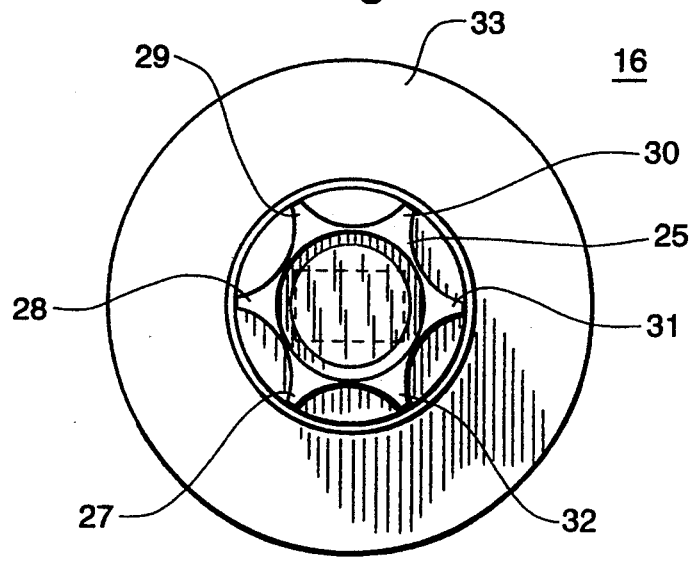
Figure 8A:
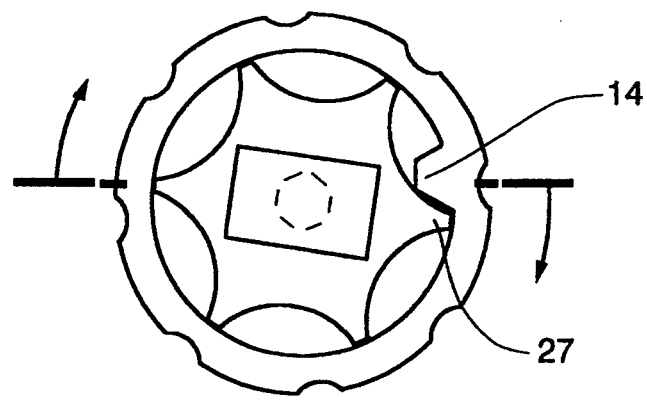
FIGS. 8a and 8b are schematic representations of the wrench tool, the plastic insert, and the single-toothed inside driving member of the ratchet at the point of achievement of the designed torque where the plastic insert tooth fails.
Figure 8B:
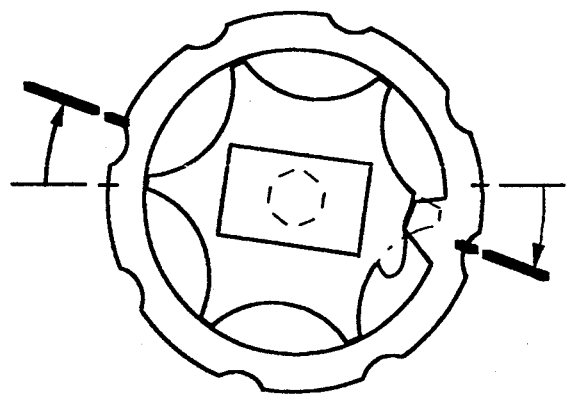

Turning now to the detailed description of the torque limit control structure, attention is directed to FIGS. 4, 5 and 6. The face 26 may be seen to be numbered 1 (start) to 6 (end). There are a plurality of 6 cams or fluted teeth 27, 28, 29, 30, 31 and 32 which correspond to the numbered positions on the face 26. Each cam functions in sequence with driver 14, FIGS. 2, 7 and 8a, to drive the tool adaptor 16. A preferred material of construction for the torque limiter would be plastic and the polyacetals are preferred and by way of a preferred example, Delrin 100. Preferred materials of construction are biocompatible and can be molded and machined. Plastics formulated to the desired limit for shearing are most preferred. In some preferred embodiments metal is a preferred material, or a metal frame, with plastic exterior. Other materials are satisfactory in many situations and in some situations other embodiments would be preferred.

It is not only the formulation of the material from which the cams are made that provides the torque limit characteristics of the cams, but also the geometry and thickness of the cams or cam flutes. The flutes are formed with a shape and depth in conjunction with the material of construction to provide the desired torque limit in the cam driver blade mechanism interface.

The cams 27, 28, 29, 30, 31 and 32 (FIG. 6) are arranged concentrically about a hub area 37 (FIG. 7) of the tool adaptor 16, projecting from the hub 37 in the same plane with the cams or teeth having their fluted faces disposed perpendicular to the plane with the curvature of the flutes aligned with the plane but the barrel of the flutes extending Perpendicular to the plane. The hub 37 is the central part of the torque limit control that would be within a continuous circle within the innermost extension of the cams where the cams merge. The hub extended 38 as depicted in FIG. 5 is the slightly enlarged area having race 35 formed in its outer surface.

The fixture aperture is centered concentrically with the torque limit controls and opens Perpendicularly to the plane in which the cams project from the hub of the torque limit control structure. Each cam is shearable upon being driven by a driver beyond a certain preset driving pressure through torque applied by a tool. A typical shear resistance would be 20 Newton-centimeters (N-cm). A preferred series of torque limit control units would provide individual torque controls 25 having varying torque shear resistances but none of the torque controls would have shears of less than 5 N-cm and none would have shears of more than 75 N-cm. More preferably the shears would be somewhere within the range of 7–50 N-cm. A series of torque regulators would typically have specific shearing resistances of 10, 20 and 30 N-cms. The appropriate torque regulator for the task would be chosen and loaded in the wrench. This would provide a very accurate approximation of the exact intended torque. Of course, in some instances it may be desired to provide torque controls having only a single torque shear resistance value and not a series of torque controls having varied torque values.

The preferred material of construction for the ratchet wrench would be stainless steel heat treated or coated with titanium nitride that will survive normal autoclaving and other sterilization procedures used in the dental operatory environment. The driver 14 is preferably made of the same stainless steel as the overall ratchet wrench 10 of which it is a part.

As seen in FIGS. 1, 2 and 7 the journaling seat ring 17 is a circular bearing projecting from the closed side of the housing into the cylindrical space and concentric with, but spaced inwardly of the outer dimensions of the inside of the cylinder of the cylindrical housing 19. The cylindrical carrier 9 is mounted in the cylindrical housing 19 with a bearing interface (roller bearings 21). The cylindrical carrier or drive sleeve 9 is open at both sides and the lip 15 projects from the inside surface between the driver 14 and one open side thereof. The rotating driver 14 carried by and projecting from the inside surface of the hollow cylindrical carrier 9 can be rotated around the circular path defined by the circular cylindrical space defined by the circular housing part 39 by shearing the cams.

To secure the torque regulator 25 within the hollow housing 39 the locator stabilizer groove race channel 35 fits down over and seats on the journaling seat ring 17 and the snap groove race channel 36 snaps over snap retention journaling rim ring 15. Looking at FIGS. 1, 2, 6, 7, 8a and 8b, it will be observed that the fluting and spacing of the cams provides a space or volume within the hollow cylindrical housing 39 of the wrench 10 to retain any sheared materials. Any sheared material would be retained within the wrench by the back face 33 which forms a closure of the open side of the wrench housing 39 with the sleeve 9 and the inside floors 19 and 20 which close the other side of the housing. The extended back face 33 which extends from one end of the hub 37 spaced outwardly on the end of the hub from the groove 36 also forms a closure with the outer face 18 of the hollow cylindrical housing 39 of wrench 10 closing in the bearing race 22.

It can also be observed that a closure to seal any sheared material within the wrench 10 is formed by the snap groove 36 on the hub extended 38 mating with the snap ring rim or lip 15. Thus the area of the wrench that might contain any material shearing from the cams has a double closure and the ball bearing race has a single closure.

Turning now to the function of the torque limit control system of the preferred embodiment described in detail, look at FIGS. 4, 7, 8a and 8b. A tool adaptor-torque limit controller 16 is chosen to yield the desired torque limit. Preferably the dentist/prosthodontist will have a selection of torque limiting controllers available with different torque limit valves. A preferred method of coding the valves for different torque limits is by color coding. A preferred color coding is by forming the torque limit controller out of plastics that contain different color pigments.

Having chosen the desired torque limit controller 16, the controller is snapped into position in the ratchet wrench 10 with the start position 1 indexed to a marking not shown. Then in a preferred sequence of set-up, the tool 24 is positioned in the tool holder 23. It is preferred that the tool have a standard mounting base 40 so that the tool mount 23 can be standard. Thus there would be a series of different tools each having a universal mounting base 40. However, in some applications it may be preferred to vary the mounting bases and mounts so that there is further assurance against using the wrong torque limit control or for other reasons. Of course, in the usual instance a dental assistant will have assembled the wrench 10, torque limit controller 16, and tool and laid out all of the dental assemblings to be positioned before the dentist/prosthodontist begins the patient's treatment. In one typical procedure a number of abutment bases will already have been implanted in the patient's oral bone structure. Typically not more than 6 bases are involved in a single treatment. The prosthodontist is now in a position to position up to six copings on respective bases and using the assembled torque limited wrench to sequentially tighten each of the up to 6 copings without interrupting the procedure to reload the wrench.

Each torque limit control cam 27-32 will operate with the driver 14 as a mechanism to provide a preset torque. As the torque limit is reached for each coping the driver 14 will shear a respective cam, FIG. 8b. This shearing will be felt by the prosthodontist who can then immediately move the torque limited wrench to the next coping. This limits the time of treatment, improving the treatment and aids patient comfort.

It is believed that the shearing action of the present invention is superior to a breaking or mechanical release action because, on balance, a shearing action should be less sudden and jerking. Particularly with the preferred embodiment of the present invention where there are multiple torque limit controls in a single torque limit controller shearing is believed advantageous. Dentists/prosthodontists develop a feel for small differences in resistance. Of course, the present invention in its broader aspects is not limited to having multiple torque limit controls in a single torque limit controller although a multiple controller is the preferred embodiment.

It is claimed:

1. A dental tightening torque limit tool holder comprising a tool fixture, a hub and a plurality of torque limit controls, each of said torque limit controls is a tooth, said teeth project concentrically from said hub in the same plane with each tooth having a face disposed perpendicular to said plane, said tool fixture, hub and plurality of torque limit controls being integral.

2. The dental tool holder of claim 1 wherein the tool fixture and the torque limit control are unitary.

3. The dental tool holder of claim 1 wherein said face of each of said teeth is in the form of a flute having its curvature aligned with said plane but its barrel extending perpendicular to said plane.

4. The dental tool holder of claim 3 wherein said flutes are shearable upon being driven by a driver beyond a certain driving pressure through torquing applied by a tool.

5. The dental tool holder of claim 4 comprising plastic and said tool fixture centered concentrically with said torque limit controls and opening perpendicularly to said plane for receipt of a tool and said plurality of torque limit controls being six.

6. A dental prosthodontic tool torque regulator comprising a plurality of cams each of which has a shear resistance within the range of 5 to 75 N-cm and comprising an arcuate face, said arcuate faces positioned to be engaged by a driver sequentially for being driven and then sheared sequentially when the torque resistance reaches the specified level.

7. The dental prosthodontic tool torque regulator of claim 6 wherein said cams each have a shear resistance within the range of 7 to 50 N-cm.

8. The dental prosthodontic tool torque regulator of claim 6 wherein the arc of each of said acute faces is aligned so that the inside of the arc is engaged by the driver.

9. The dental prosthodontic tool torque regulator of claim 8 wherein said plurality of cams are arranged concentricly about a hub.

10. The dental prosthodontic tool torque regulator of claim 6 wherein said cams are unitary with a hub and made of a unitary material with said hub and said hub comprising a tool mount.

11. A wrench for driving and tightening components in a dental prosthodontic restoration comprising a hollow cylindrical housing open at one side and closed at the other side, a circular bearing projecting from said closed side of said housing into the cylindrical open space and concentric with, but spaced inwardly of the outer dimensions of the inside of the cylinder of said cylindrical open space; a hollow rotating cylindrical carrier mounted in said cylindrical housing with a bearing interface with said cylindrical housing and rotating around a circular path defined by said cylindrical housing, said cylindrical carrier open at both sides exposing said circular bearing to said open side of said hollow cylindrical housing, and a driver projecting from an inside surface of said cylindrical carrier.

12. A wrench for driving and tightening components in a dental prosthodontic restoration comprising a hollow cylindrical housing, a cylindrical carrier carrying a driver that rotates around a circular path defined by the circular space defined by said hollow cylindrical housing, and a torque limit control structure comprising a hub positioned concentrically within said housing and a plurality of torque limiting cams spaced evenly concentrically around said hub and projecting therefrom and positioned to come into driven engagement with said driver, each of said cams having the same resistance to being sheared when driven to a preset torque by said driver, and said hub comprising a groove at one end and an extended backface extending at said one end spaced outwardly on said end from said groove and said hollow cylindrical housing having an outer face and said cylindrical carrier having a lip thereon fitting in said groove forming a closure to seal any sheared materials within said hollow cylindrical housing, said outer face of said housing engaged by said extended back face to form a second closure to retain any sheared material in said wrench.

13. A dental prosthodontic torque regulator wrench comprising a hollow cylindrical housing having an outer face, a cylindrical carrier rotating on ball bearings within said housing, and a torque regulator, said torque regulator comprising a hub and a plurality of cams spaced evenly concentrically about said hub and projecting from said hub, each cam having the same resistance to being sheared, said hub comprising a snap groove and an extended backface extending from said torque regulator at one end of said hub and said cylindrical carrier having a snap ring rim which snaps with said snap groove forming a closure to seal any sheared materials within said wrench, said outer face of said housing engaged by said extended back face to form a second closure to seal any sheared material in said wrench and forming a closure for the ball bearings.

* * * * *